US012226123B2

(12) United States Patent
Blanchard

(10) Patent No.: US 12,226,123 B2
(45) Date of Patent: Feb. 18, 2025

(54) SAFETY MECHANISM

(71) Applicant: Bard Access Systems, Inc., Salt Lake City, UT (US)

(72) Inventor: Daniel B. Blanchard, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 739 days.

(21) Appl. No.: 17/378,304

(22) Filed: Jul. 16, 2021

(65) Prior Publication Data

US 2022/0015801 A1 Jan. 20, 2022

Related U.S. Application Data

(60) Provisional application No. 63/053,356, filed on Jul. 17, 2020.

(51) Int. Cl.
*A61B 17/34* (2006.01)
(52) U.S. Cl.
CPC ...... *A61B 17/3472* (2013.01); *A61B 17/3423* (2013.01); *A61B 17/3496* (2013.01); *A61B 2017/347* (2013.01)
(58) Field of Classification Search
CPC ............ A61B 17/3472; A61B 17/3423; A61B 17/3496; A61B 17/3494; A61B 17/16;
(Continued)

(56) References Cited

U.S. PATENT DOCUMENTS 2,773,501 A 12/1956 Young
3,071,135 A 1/1963 Baldwin et al.
(Continued)

FOREIGN PATENT DOCUMENTS

EP 0232600 A1 8/1987
EP 0548612 A1 6/1993
(Continued)

OTHER PUBLICATIONS

PCT/US2021/042040 filed Jul. 16, 2021 International Search Report and Written Opinion dated Oct. 4, 2021.
(Continued)

*Primary Examiner* — Nathan R Price
*Assistant Examiner* — Haden Matthew Ritchie
(74) *Attorney, Agent, or Firm* — Rutan & Tucker LLP

(57) ABSTRACT

A safety mechanism is disclosed configured for shielding a distal tip of an elongate medical device. The safety mechanism includes a sheath having a body defining a lumen extending axially and including a shroud extending axially and having one or more sheath apertures disposed therethrough. The safety mechanism further includes a clip, comprising one or more arms, each including a tab, a plate, and a grip, the tab including a keyhole aperture. The first arm and the second arm configured to transition between a first configuration and a second configuration, and an elongate biasing member extending from the first arm to the second arm and configured to bias the first arm and the second arm towards the second configuration. Transitioning from the first configuration to the second configuration disengages the sheath from a needle hub and engages the sheath with a tip of the elongate medical device.

26 Claims, 6 Drawing Sheets

(58) Field of Classification Search
CPC .............. A61B 17/00; A61B 17/1633; A61B 2017/347; A61B 2090/0801
See application file for complete search history.

(56) References Cited

U.S. PATENT DOCUMENTS

| | | | |
|---|---|---|---|
| 3,166,189 A | 1/1965 | Disston |
| 3,329,261 A | 7/1967 | Serany, Jr. et al. |
| D222,312 S | 10/1971 | Kurtz et al. |
| 3,802,555 A | 4/1974 | Grasty et al. |
| 3,815,605 A | 6/1974 | Schmidt et al. |
| 3,991,765 A | 11/1976 | Cohen |
| 4,010,737 A | 3/1977 | Vilaghy et al. |
| 4,153,160 A | 5/1979 | Leigh |
| 4,226,328 A | 10/1980 | Beddow |
| 4,266,555 A | 5/1981 | Jamshidi |
| 4,314,565 A | 2/1982 | Lee |
| 4,383,530 A | 5/1983 | Bruno |
| 4,501,363 A | 2/1985 | Isbey, Jr. |
| 4,595,102 A | 6/1986 | Cianci et al. |
| 4,838,282 A | 6/1989 | Strasser et al. |
| 4,889,529 A | 12/1989 | Haindl |
| 4,925,448 A | 5/1990 | Bazaral |
| 4,952,207 A | 8/1990 | Lemieux |
| 4,964,854 A | 10/1990 | Luther |
| 4,969,870 A | 11/1990 | Kramer et al. |
| 5,040,542 A | 8/1991 | Gray |
| 5,042,558 A | 8/1991 | Hussey et al. |
| 5,053,017 A | 10/1991 | Chamuel |
| 5,098,391 A | 3/1992 | Pantages et al. |
| 5,122,114 A | 6/1992 | Miller et al. |
| 5,207,697 A | 5/1993 | Carusillo et al. |
| 5,263,939 A | 11/1993 | Wortrich |
| 5,290,267 A | 3/1994 | Zimmermann |
| 5,312,364 A | 5/1994 | Jacobs |
| 5,322,163 A | 6/1994 | Foos |
| 5,332,398 A | 7/1994 | Miller et al. |
| 5,364,367 A | 11/1994 | Banks et al. |
| 5,372,583 A | 12/1994 | Roberts et al. |
| 5,406,940 A | 4/1995 | Melzer et al. |
| 5,451,210 A | 9/1995 | Kramer et al. |
| 5,525,314 A | 6/1996 | Hurson |
| 5,554,154 A | 9/1996 | Rosenberg |
| 5,575,780 A | 11/1996 | Saito |
| 5,591,188 A | 1/1997 | Waisman |
| 5,601,559 A | 2/1997 | Melker et al. |
| 5,688,249 A | 11/1997 | Chang et al. |
| 5,746,720 A | 5/1998 | Stouder, Jr. |
| 5,772,678 A | 6/1998 | Thomason et al. |
| 5,779,708 A | 7/1998 | Wu |
| 5,807,275 A | 9/1998 | Jamshidi |
| 5,810,738 A | 9/1998 | Thomas, II |
| 5,810,826 A | 9/1998 | Åkerfeldt et al. |
| 5,817,052 A | 10/1998 | Johnson et al. |
| 5,853,393 A | 12/1998 | Bogert |
| 5,868,684 A | 2/1999 | Åkerfeldt et al. |
| 5,868,711 A | 2/1999 | Kramer et al. |
| 5,871,470 A | 2/1999 | McWha |
| 5,885,293 A | 3/1999 | McDevitt |
| 5,927,976 A | 7/1999 | Wu |
| 5,947,890 A | 9/1999 | Spencer et al. |
| 5,960,797 A | 10/1999 | Kramer et al. |
| 5,967,143 A | 10/1999 | Klappenberger |
| 5,990,382 A | 11/1999 | Fox |
| 6,012,586 A | 1/2000 | Misra |
| 6,068,121 A | 5/2000 | McGlinch |
| 6,117,108 A | 9/2000 | Woehr et al. |
| 6,135,769 A | 10/2000 | Kwan |
| 6,210,373 B1 | 4/2001 | Allmon |
| 6,210,376 B1 | 4/2001 | Grayson |
| 6,228,088 B1 | 5/2001 | Miller et al. |
| 6,247,928 B1 | 6/2001 | Meller et al. |
| 6,273,715 B1 | 8/2001 | Meller et al. |
| 6,419,490 B1 | 7/2002 | Kitchings Weathers, Jr. |
| 6,458,117 B1 | 10/2002 | Pollins, Sr. |
| 6,527,778 B2 | 3/2003 | Athanasiou et al. |
| 6,602,214 B2 | 8/2003 | Heinz et al. |
| 6,626,887 B1 | 9/2003 | Wu |
| 6,629,959 B2 | 10/2003 | Kuracina et al. |
| 6,641,395 B2 | 11/2003 | Kumar et al. |
| 6,652,490 B2 | 11/2003 | Howell |
| 6,692,471 B2 | 2/2004 | Boudreaux |
| 6,761,726 B1 | 7/2004 | Findlay et al. |
| 6,814,734 B2 | 11/2004 | Chappuis et al. |
| 6,830,562 B2 | 12/2004 | Mogensen et al. |
| 6,875,219 B2 | 4/2005 | Arramon et al. |
| 6,905,486 B2 | 6/2005 | Gibbs |
| 6,916,292 B2 | 7/2005 | Morawski et al. |
| 6,984,213 B2 | 1/2006 | Horner et al. |
| 6,991,096 B2 | 1/2006 | Gottlieb et al. |
| 6,997,907 B2 | 2/2006 | Safabash et al. |
| 7,112,191 B2 | 9/2006 | Daga |
| 7,135,031 B2 | 11/2006 | Flint |
| 7,179,244 B2 | 2/2007 | Smith et al. |
| 7,214,208 B2 | 5/2007 | Vaillancourt et al. |
| 7,278,987 B2 | 10/2007 | Solazzo |
| 7,347,838 B2 | 3/2008 | Kulli |
| 7,347,840 B2 | 3/2008 | Findlay et al. |
| 7,399,306 B2 | 7/2008 | Reiley et al. |
| 7,407,493 B2 | 8/2008 | Cane' |
| 7,410,053 B2 | 8/2008 | Bowen et al. |
| 7,434,687 B2 | 10/2008 | Itou et al. |
| 7,458,954 B2 | 12/2008 | Ferguson et al. |
| 7,513,888 B2 | 4/2009 | Sircom et al. |
| 7,530,965 B2 | 5/2009 | Villa et al. |
| 7,534,227 B2 | 5/2009 | Kulli |
| 7,569,033 B2 | 8/2009 | Greene et al. |
| 7,582,102 B2 | 9/2009 | Heinz et al. |
| 7,588,559 B2 | 9/2009 | Aravena et al. |
| 7,658,725 B2 | 2/2010 | Bialecki et al. |
| 7,670,328 B2 | 3/2010 | Miller |
| 7,699,807 B2 | 4/2010 | Faust et al. |
| 7,699,850 B2 | 4/2010 | Miller |
| 7,736,332 B2 | 6/2010 | Carlyon et al. |
| 7,743,918 B2 | 6/2010 | Itou et al. |
| 7,749,225 B2 | 7/2010 | Chappuis et al. |
| 7,798,994 B2 | 9/2010 | Brimhall |
| 7,811,260 B2 | 10/2010 | Miller et al. |
| 7,815,642 B2 | 10/2010 | Miller |
| 7,828,773 B2 | 11/2010 | Swisher et al. |
| 7,828,774 B2 | 11/2010 | Harding et al. |
| 7,833,204 B2 | 11/2010 | Picha |
| 7,842,038 B2 | 11/2010 | Haddock et al. |
| 7,850,620 B2 | 12/2010 | Miller et al. |
| 7,850,650 B2 | 12/2010 | Breitweiser |
| D633,199 S | 2/2011 | MacKay et al. |
| 7,899,528 B2 | 3/2011 | Miller et al. |
| 7,900,549 B2 | 3/2011 | Kobayashi |
| 7,905,857 B2 | 3/2011 | Swisher |
| 7,951,089 B2 | 5/2011 | Miller |
| 7,955,297 B2 | 6/2011 | Radmer et al. |
| 7,972,339 B2 | 7/2011 | Nassiri et al. |
| 7,976,498 B2 | 7/2011 | Swisher et al. |
| 7,976,502 B2 | 7/2011 | Baid |
| 8,038,664 B2 | 10/2011 | Miller et al. |
| 8,043,253 B2 | 10/2011 | Kraft et al. |
| 8,043,265 B2 | 10/2011 | Abe et al. |
| 8,096,973 B2 | 1/2012 | Snow et al. |
| 8,142,365 B2 | 3/2012 | Miller |
| 8,152,771 B2 | 4/2012 | Mogensen et al. |
| 8,162,904 B2 | 4/2012 | Takano et al. |
| 8,167,899 B2 | 5/2012 | Justis et al. |
| 8,231,547 B2 | 7/2012 | Deck et al. |
| 8,235,945 B2 | 8/2012 | Baid |
| 8,240,468 B2 | 8/2012 | Wilkinson et al. |
| 8,246,584 B2 | 8/2012 | Aravena et al. |
| 8,273,053 B2 | 9/2012 | Saltzstein |
| 8,292,891 B2 | 10/2012 | Browne et al. |
| 8,308,693 B2 | 11/2012 | Miller et al. |
| 8,333,769 B2 | 12/2012 | Browne et al. |
| 8,356,598 B2 | 1/2013 | Rumsey |
| 8,357,163 B2 | 1/2013 | Sidebotham et al. |
| 8,388,623 B2 | 3/2013 | Browne et al. |
| 8,414,539 B1 | 4/2013 | Kuracina et al. |

(56) References Cited

U.S. PATENT DOCUMENTS

| | | |
|---|---|---|
| 8,419,683 B2 | 4/2013 | Miller et al. |
| 8,480,632 B2 | 7/2013 | Miller et al. |
| 8,480,672 B2 | 7/2013 | Browne et al. |
| 8,486,027 B2 | 7/2013 | Findlay et al. |
| 8,506,568 B2 | 8/2013 | Miller |
| 8,529,576 B2 | 9/2013 | Krueger et al. |
| 8,535,271 B2 | 9/2013 | Fuchs et al. |
| 8,562,615 B2 | 10/2013 | Browne et al. |
| 8,584,849 B2 | 11/2013 | McCaffrey |
| 8,641,715 B2 | 2/2014 | Miller |
| 8,647,257 B2 | 2/2014 | Jansen et al. |
| 8,656,929 B2 | 2/2014 | Miller et al. |
| 8,657,790 B2 | 2/2014 | Tal et al. |
| 8,662,306 B2 | 3/2014 | Agrawal |
| 8,663,231 B2 | 3/2014 | Browne et al. |
| 8,668,698 B2 | 3/2014 | Miller et al. |
| 8,684,978 B2 | 4/2014 | Miller et al. |
| 8,690,791 B2 | 4/2014 | Miller |
| 8,715,287 B2 | 5/2014 | Miller |
| 8,758,383 B2 | 6/2014 | Geist |
| 8,771,230 B2 | 7/2014 | White et al. |
| 8,801,663 B2 | 8/2014 | Woehr |
| 8,812,101 B2 | 8/2014 | Miller et al. |
| 8,814,835 B2 | 8/2014 | Baid |
| 8,828,001 B2 | 9/2014 | Stearns et al. |
| 8,870,872 B2 | 10/2014 | Miller |
| 8,893,883 B2 | 11/2014 | Valaie et al. |
| D720,471 S | 12/2014 | Angel et al. |
| 8,936,575 B2 | 1/2015 | Moulton |
| 8,944,069 B2 | 2/2015 | Miller et al. |
| 8,974,410 B2 | 3/2015 | Miller et al. |
| 8,998,848 B2 | 4/2015 | Miller et al. |
| 9,072,543 B2 | 7/2015 | Miller et al. |
| 9,078,637 B2 | 7/2015 | Miller |
| 9,131,925 B2 | 9/2015 | Kraft et al. |
| 9,149,625 B2 | 10/2015 | Woehr et al. |
| 9,173,679 B2 | 11/2015 | Tzachar et al. |
| 9,186,217 B2 | 11/2015 | Goyal |
| 9,226,756 B2 | 1/2016 | Teisen et al. |
| 9,278,195 B2 | 3/2016 | Erskine |
| 9,295,487 B2 | 3/2016 | Miller et al. |
| 9,302,077 B2 | 4/2016 | Domonkos et al. |
| 9,314,232 B2 | 4/2016 | Stark |
| 9,314,270 B2 | 4/2016 | Miller |
| 9,358,348 B2 | 6/2016 | Weilbacher et al. |
| 9,393,031 B2 | 7/2016 | Miller |
| 9,414,815 B2 | 8/2016 | Miller et al. |
| 9,415,192 B2 | 8/2016 | Kuracina et al. |
| 9,421,345 B2 | 8/2016 | Woehr et al. |
| 9,427,555 B2 | 8/2016 | Baid |
| 9,433,400 B2 | 9/2016 | Miller |
| 9,439,667 B2 | 9/2016 | Miller |
| 9,439,702 B2 | 9/2016 | Arthur et al. |
| 9,451,968 B2 | 9/2016 | Miller et al. |
| 9,451,983 B2 | 9/2016 | Windolf |
| 9,480,483 B2 | 11/2016 | Browne et al. |
| 9,486,604 B2 | 11/2016 | Murray et al. |
| 9,504,477 B2 | 11/2016 | Miller et al. |
| 9,545,243 B2 | 1/2017 | Miller et al. |
| 9,615,816 B2 | 4/2017 | Woodard |
| 9,615,838 B2 | 4/2017 | Nino et al. |
| 9,623,210 B2 | 4/2017 | Woehr |
| 9,636,484 B2 | 5/2017 | Baid |
| 9,681,889 B1 | 6/2017 | Greenhalgh et al. |
| 9,687,633 B2 | 6/2017 | Teoh |
| 9,717,564 B2 | 8/2017 | Miller et al. |
| 9,730,729 B2 | 8/2017 | Kilcoin et al. |
| 9,744,333 B2 | 8/2017 | Terzibashian |
| 9,782,546 B2 | 10/2017 | Woehr |
| 9,788,843 B2 | 10/2017 | Teisen et al. |
| 9,839,740 B2 | 12/2017 | Beamer et al. |
| 9,844,646 B2 | 12/2017 | Knutsson |
| 9,844,647 B2 | 12/2017 | Knutsson |
| 9,872,703 B2 | 1/2018 | Miller et al. |
| 9,883,853 B2 | 2/2018 | Woodard et al. |
| 9,895,512 B2 | 2/2018 | Kraft et al. |
| 9,962,211 B2 | 5/2018 | Csernatoni |
| 9,999,444 B2 | 6/2018 | Geist et al. |
| 10,022,464 B2 | 7/2018 | Sarphati et al. |
| 10,039,897 B2 | 8/2018 | Norris et al. |
| 10,052,111 B2 | 8/2018 | Miller et al. |
| 10,064,694 B2 | 9/2018 | Connolly |
| 10,070,933 B2 | 9/2018 | Adler et al. |
| 10,070,934 B2 | 9/2018 | Kerns et al. |
| 10,080,864 B2 | 9/2018 | Terzibashian |
| 10,092,320 B2 | 10/2018 | Morgan et al. |
| 10,106,295 B2 | 10/2018 | Lockwood |
| 10,130,343 B2 | 11/2018 | Miller et al. |
| 10,136,878 B2 | 11/2018 | Tzachar et al. |
| 10,182,878 B2 | 1/2019 | Goyal |
| 10,238,420 B2 | 3/2019 | Karve et al. |
| 10,245,010 B2 | 4/2019 | Miller et al. |
| 10,251,812 B2 | 4/2019 | Tomes et al. |
| 10,258,783 B2 | 4/2019 | Miller et al. |
| 10,314,629 B2 | 6/2019 | Park et al. |
| 10,405,938 B2 | 9/2019 | Ramsey |
| 10,441,454 B2 | 10/2019 | Tanghoej et al. |
| 10,456,149 B2 | 10/2019 | Miller |
| 10,456,497 B2 | 10/2019 | Howell et al. |
| 10,595,896 B2 | 3/2020 | Miller |
| 10,722,247 B2 | 7/2020 | Browne et al. |
| 10,893,887 B2 | 1/2021 | Blanchard |
| 2003/0060781 A1 | 3/2003 | Mogensen et al. |
| 2003/0225344 A1 | 12/2003 | Miller |
| 2003/0225411 A1 | 12/2003 | Miller |
| 2003/0229308 A1 | 12/2003 | Tsals et al. |
| 2004/0162559 A1 | 8/2004 | Arramon et al. |
| 2004/0220497 A1 | 11/2004 | Findlay et al. |
| 2004/0243135 A1 | 12/2004 | Koseki |
| 2005/0033235 A1 | 2/2005 | Flint |
| 2005/0035014 A1 | 2/2005 | Cane |
| 2005/0101912 A1 | 5/2005 | Faust et al. |
| 2005/0113866 A1 | 5/2005 | Heinz et al. |
| 2005/0148940 A1 | 7/2005 | Miller |
| 2005/0165403 A1 | 7/2005 | Miller |
| 2005/0261693 A1 | 11/2005 | Miller et al. |
| 2006/0015066 A1 | 1/2006 | Turieo et al. |
| 2006/0025723 A1 | 2/2006 | Ballarini |
| 2007/0010843 A1 | 1/2007 | Green |
| 2007/0016138 A1 | 1/2007 | Swisher et al. |
| 2007/0049945 A1 | 3/2007 | Miller |
| 2007/0191772 A1 | 8/2007 | Wojcik |
| 2007/0270775 A1 | 11/2007 | Miller et al. |
| 2008/0086142 A1 | 4/2008 | Kohm et al. |
| 2008/0119759 A1 | 5/2008 | McLain |
| 2008/0119821 A1 | 5/2008 | Agnihotri et al. |
| 2008/0140014 A1 | 6/2008 | Miller et al. |
| 2008/0154304 A1 | 6/2008 | Crawford et al. |
| 2008/0208136 A1 | 8/2008 | Findlay et al. |
| 2008/0215056 A1 | 9/2008 | Miller et al. |
| 2008/0221580 A1 | 9/2008 | Miller et al. |
| 2008/0257359 A1 | 10/2008 | Rumsey |
| 2009/0048575 A1 | 2/2009 | Waters |
| 2009/0054808 A1 | 2/2009 | Miller |
| 2009/0093830 A1 | 4/2009 | Miller |
| 2009/0105775 A1 | 4/2009 | Mitchell et al. |
| 2009/0118639 A1 | 5/2009 | Moos et al. |
| 2009/0204024 A1 | 8/2009 | Miller |
| 2009/0228014 A1 | 9/2009 | Stearns et al. |
| 2009/0306697 A1 | 12/2009 | Fischvogt |
| 2010/0030105 A1 | 2/2010 | Noishiki et al. |
| 2010/0082033 A1 | 4/2010 | Germain |
| 2010/0152616 A1 | 6/2010 | Beyhan et al. |
| 2010/0185161 A1 | 7/2010 | Pellegrino et al. |
| 2010/0204649 A1 | 8/2010 | Miller et al. |
| 2010/0280410 A1 | 11/2010 | Moos et al. |
| 2010/0286607 A1 | 11/2010 | Saltzstein |
| 2010/0298830 A1 | 11/2010 | Browne et al. |
| 2010/0298831 A1 | 11/2010 | Browne et al. |
| 2010/0312246 A1 | 12/2010 | Browne et al. |
| 2011/0004163 A1 | 1/2011 | Vaidya |
| 2011/0028976 A1 | 2/2011 | Miller |
| 2011/0137253 A1 | 6/2011 | Simonton et al. |
| 2012/0041454 A1 | 2/2012 | Johnstone |

(56) References Cited

U.S. PATENT DOCUMENTS

| | | |
|---|---|---|
| 2012/0202180 A1 | 8/2012 | Stock et al. |
| 2012/0203154 A1 | 8/2012 | Tzachar |
| 2013/0030439 A1 | 1/2013 | Browne et al. |
| 2013/0041345 A1 | 2/2013 | Kilcoin et al. |
| 2013/0072938 A1 | 3/2013 | Browne et al. |
| 2013/0079720 A1 | 3/2013 | Finnestad et al. |
| 2013/0102924 A1 | 4/2013 | Findlay et al. |
| 2013/0158484 A1 | 6/2013 | Browne et al. |
| 2013/0178807 A1 | 7/2013 | Baid |
| 2013/0331840 A1 | 12/2013 | Teisen et al. |
| 2014/0039400 A1 | 2/2014 | Browne et al. |
| 2014/0046327 A1 | 2/2014 | Tzachar et al. |
| 2014/0074102 A1 | 3/2014 | Mandeen et al. |
| 2014/0081281 A1 | 3/2014 | Felder |
| 2014/0142577 A1 | 5/2014 | Miller |
| 2014/0262408 A1 | 9/2014 | Woodard |
| 2014/0262880 A1 | 9/2014 | Yoon |
| 2014/0276205 A1 | 9/2014 | Miller et al. |
| 2014/0276206 A1 | 9/2014 | Woodward et al. |
| 2014/0276366 A1 | 9/2014 | Bourne et al. |
| 2014/0276471 A1 | 9/2014 | Emery et al. |
| 2014/0276833 A1 | 9/2014 | Larsen et al. |
| 2014/0276839 A1 | 9/2014 | Forman et al. |
| 2014/0276927 A1 | 9/2014 | Barker |
| 2014/0343454 A1 | 11/2014 | Miller et al. |
| 2014/0343497 A1 | 11/2014 | Baid |
| 2015/0011941 A1 | 1/2015 | Saeki |
| 2015/0126931 A1 | 5/2015 | Holm et al. |
| 2015/0127006 A1 | 5/2015 | Miller |
| 2015/0196737 A1 | 7/2015 | Baid |
| 2015/0223786 A1 | 8/2015 | Morgan et al. |
| 2015/0230823 A1 | 8/2015 | Morgan et al. |
| 2015/0238733 A1 | 8/2015 | bin Abdulla |
| 2015/0342615 A1 | 12/2015 | Keinan et al. |
| 2015/0342756 A1 | 12/2015 | Bays et al. |
| 2015/0351797 A1 | 12/2015 | Miller et al. |
| 2015/0366569 A1 | 12/2015 | Miller |
| 2016/0022282 A1 | 1/2016 | Miller et al. |
| 2016/0058432 A1 | 3/2016 | Miller |
| 2016/0066954 A1 | 3/2016 | Miller et al. |
| 2016/0106441 A1 | 4/2016 | Teisen et al. |
| 2016/0136410 A1 | 5/2016 | Aklog et al. |
| 2016/0183974 A1 | 6/2016 | Miller |
| 2016/0228676 A1 | 8/2016 | Glithero et al. |
| 2016/0235949 A1 | 8/2016 | Baid |
| 2016/0354539 A1 | 12/2016 | Tan et al. |
| 2016/0361519 A1 | 12/2016 | Teoh et al. |
| 2017/0021138 A1 | 1/2017 | Sokolski |
| 2017/0043135 A1 | 2/2017 | Knutsson |
| 2017/0056122 A1 | 3/2017 | Ramsey |
| 2017/0105763 A1 | 4/2017 | Karve et al. |
| 2017/0136217 A1 | 5/2017 | Riesenberger et al. |
| 2017/0143395 A1 | 5/2017 | Park et al. |
| 2017/0151419 A1 | 6/2017 | Sonksen |
| 2017/0156740 A9 | 6/2017 | Stark |
| 2017/0156751 A1 | 6/2017 | Csernatoni |
| 2017/0209129 A1 | 7/2017 | Fagundes et al. |
| 2017/0303962 A1 | 10/2017 | Browne et al. |
| 2017/0303963 A1 | 10/2017 | Kilcoin et al. |
| 2018/0092662 A1 | 4/2018 | Rioux et al. |
| 2018/0116642 A1 | 5/2018 | Woodard et al. |
| 2018/0116693 A1 | 5/2018 | Blanchard et al. |
| 2018/0117262 A1 | 5/2018 | Islam |
| 2018/0125465 A1 | 5/2018 | Muse et al. |
| 2018/0154112 A1 | 6/2018 | Chan et al. |
| 2018/0206933 A1 | 7/2018 | Healey et al. |
| 2018/0221564 A1 | 8/2018 | Patel et al. |
| 2018/0236182 A1 | 8/2018 | Charlebois et al. |
| 2018/0256209 A1* | 9/2018 | Muse ............... A61M 5/3273 |
| 2019/0021807 A1 | 1/2019 | Barnell et al. |
| 2019/0060607 A1 | 2/2019 | Yabu et al. |
| 2019/0076132 A1 | 3/2019 | Tzachar et al. |
| 2019/0125404 A1 | 5/2019 | Shippert |
| 2019/0150953 A1 | 5/2019 | Budyansky et al. |
| 2019/0151606 A1 | 5/2019 | Mottola et al. |
| 2019/0201053 A1 | 7/2019 | Ben Mocha et al. |
| 2019/0282244 A1 | 9/2019 | Muse |
| 2019/0328370 A1 | 10/2019 | Muse |
| 2019/0343556 A1 | 11/2019 | Coppedge et al. |
| 2021/0093358 A1 | 4/2021 | Lindekugel et al. |
| 2021/0137558 A1 | 5/2021 | Lindekugel |
| 2024/0050126 A1 | 2/2024 | Blanchard |

FOREIGN PATENT DOCUMENTS

| | | |
|---|---|---|
| WO | 1997024151 A1 | 7/1997 |
| WO | 1998052638 A3 | 2/1999 |
| WO | 2004000408 A1 | 12/2003 |
| WO | 2004073500 A2 | 9/2004 |
| WO | 2005/046769 A2 | 5/2005 |
| WO | 05041790 A2 | 5/2005 |
| WO | 2005053506 A2 | 6/2005 |
| WO | 2005072625 A2 | 8/2005 |
| WO | 2006/047737 A2 | 5/2006 |
| WO | 2007018809 A2 | 2/2007 |
| WO | 2008002961 A2 | 1/2008 |
| WO | 2008016757 A2 | 2/2008 |
| WO | 2008033871 A2 | 3/2008 |
| WO | 2008033872 A2 | 3/2008 |
| WO | 2008033873 A2 | 3/2008 |
| WO | 2008033874 A2 | 3/2008 |
| WO | 2008054894 A2 | 5/2008 |
| WO | 2008086258 A1 | 7/2008 |
| WO | 2008124206 A2 | 10/2008 |
| WO | 2008124463 A2 | 10/2008 |
| WO | 2008130893 A1 | 10/2008 |
| WO | 2008134355 A2 | 11/2008 |
| WO | 2008144379 A2 | 11/2008 |
| WO | 2009070896 A1 | 6/2009 |
| WO | 2010043043 A2 | 4/2010 |
| WO | 2011097311 A2 | 8/2011 |
| WO | 2011139294 A1 | 11/2011 |
| WO | 2013009901 A2 | 1/2013 |
| WO | 2013173360 A1 | 11/2013 |
| WO | 2014142948 A1 | 9/2014 |
| WO | 2014144239 A1 | 9/2014 |
| WO | 2014144262 A1 | 9/2014 |
| WO | 2014144489 A2 | 9/2014 |
| WO | 2014144757 A1 | 9/2014 |
| WO | 2014144797 A1 | 9/2014 |
| WO | 2015/177612 A1 | 11/2015 |
| WO | 2016033016 A1 | 3/2016 |
| WO | 16053834 A1 | 4/2016 |
| WO | 2016163939 A1 | 10/2016 |
| WO | 18006045 A1 | 1/2018 |
| WO | 2018025094 A1 | 2/2018 |
| WO | 2018058036 A1 | 3/2018 |
| WO | 2018075694 A1 | 4/2018 |
| WO | 18098086 A1 | 5/2018 |
| WO | 2018165334 A1 | 9/2018 |
| WO | 2018165339 A1 | 9/2018 |
| WO | 2019051343 A1 | 3/2019 |
| WO | 2019051412 A1 | 3/2019 |
| WO | 2019164990 A1 | 8/2019 |
| WO | 2019/215705 A1 | 11/2019 |
| WO | 2020/012051 A1 | 1/2020 |
| WO | 2021/062215 A1 | 4/2021 |
| WO | 2021173649 A1 | 9/2021 |

OTHER PUBLICATIONS

U.S. Appl. No. 17/033,093, filed Sep. 25, 2020 Non-Final Office Action dated Mar. 2, 2023.
U.S. Appl. No. 17/033,093, filed Sep. 25, 2020 Restriction Requirement dated Nov. 15, 2022.
U.S. Appl. No. 17/152,509, filed Jan. 19, 2021 Non-Final Office Action dated May 4, 2023.
U.S. Appl. No. 17/183,820, filed Feb. 24, 2021 Restriction Requirement dated Feb. 13, 2023.
EP 17861304.8 filed Apr. 16, 2019 Extended European Search Report filed Jul. 28, 2020.
EP 17864208.8 filed May 24, 2019 Extended European Search Report filed May 19, 2020.

(56) References Cited

OTHER PUBLICATIONS

PCT/US 17/57270 filed Oct. 18, 2017 International Search Report and Written Opinion dated Jan. 12, 2018.
PCT/US2017/058863 filed Oct. 27, 2017 International Search Report and Written Opinion dated Jan. 29, 2018.
PCT/US2018/021398 filed Mar. 7, 2018 International search report and written opinion dated May 21, 2018.
PCT/US2020/052809 filed Sep. 25, 2020 International Search Report and Written Opinion dated Jan. 5, 2021.
U.S. Appl. No. 15/796,471, filed Oct. 27, 2017 Advisory Action dated Jun. 15, 2020.
U.S. Appl. No. 15/796,471, filed Oct. 27, 2017 Final Office Action dated Apr. 23, 2020.
U.S. Appl. No. 15/796,471, filed Oct. 27, 2017 Non-Final Office Action dated Oct. 30, 2019.
U.S. Appl. No. 15/796,471, filed Oct. 27, 2017 Notice of Allowance dated Jun. 15, 2020.
U.S. Appl. No. 15/796,471, filed Oct. 27, 2017 Restriction Requirement dated Jul. 8, 2019.
PCT/US2021/019388 filed Feb. 24, 2021 International Search Report and Written Opinion dated May 17, 2021.
U.S. Appl. No. 17/033,093, filed Sep. 25, 2020 Final Office Action dated Feb. 15, 2024.
U.S. Appl. No. 17/033,093, filed Sep. 25, 2020 Non-Final Office Action dated Nov. 8, 2023.
U.S. Appl. No. 17/033,093, filed Sep. 25, 2020 Notice of Allowance dated Apr. 30, 2024.
U.S. Appl. No. 17/183,820, filed Feb. 24, 2021 Advisory Action dated Nov. 2, 2023.
U.S. Appl. No. 17/183,820, filed Feb. 24, 2021 Non-Final Office Action dated Dec. 27, 2023.
EP 20868558.6 filed Apr. 21, 2022 Extended European Search Report dated Aug. 11, 2023.
U.S. Appl. No. 17/033,093, filed Sep. 25, 2020 Advisory Action dated Oct. 4, 2023.
U.S. Appl. No. 17/033,093, filed Sep. 25, 2020 Final Office Action dated Sep. 8, 2023.
U.S. Appl. No. 17/152,509, filed Jan. 19, 2021 Notice of Allowance dated Sep. 7, 2023.
U.S. Appl. No. 17/183,820, filed Feb. 24, 2021 Final Office Action dated Sep. 28, 2023.
U.S. Appl. No. 17/183,820, filed Feb. 24, 2021 Non Final Office Action dated May 30, 2023.
U.S. Appl. No. 17/183,820, filed Feb. 24, 2021 Advisory Action dated Jul. 26, 2024.
U.S. Appl. No. 17/183,820, filed Feb. 24, 2021 Final Office Action dated May 29, 2024.
U.S. Appl. No. 17/183,820, filed Feb. 24, 2021 Notice of Allowance dated Aug. 28, 2024.

* cited by examiner

SAFETY MECHANISM

PRIORITY

This application claims the benefit of priority to U.S. Provisional Application No. 63/053,356, filed Jul. 17, 2020, which is incorporated by reference in its entirety into this application.

SUMMARY

Intraosseous access systems can be configured to penetrate the skin, underlying tissues, and bone cortex to access the medullary cavity of the bone and provide fluid communication therewith. Such intraosseous access systems use an obturator disposed within a needle lumen to prevent tissue or bone fragments from entering the needle lumen and obstructing the fluid pathway. Once the needle has accessed the medullary cavity, the obturator can be removed from the needle assembly. Removal of the obturator raises the risk of accidental stick injuries by the obturator tip. A safety device can be used to significantly reduce the risk of accidental stick injuries. Current safety mechanisms have multiple components that require precise machining leading to increased manufacturing complexity and associated costs. Further, the drag or activation forces can be easily imbalanced leading to failure of the device.

What is needed therefore, is a safety mechanism that has a simplified construction reducing manufacturing complexity and associated costs, improved deployment reliability, and provide a more secure engagement between the obturator tip and a protective sheath. Embodiments disclosed herein include a safety mechanism and associated methods thereof to address the foregoing.

Disclosed herein is a safety mechanism including, an elongate medical device having a shaft extending along a longitudinal axis and defining a first outer diameter, the shaft including a notch extending annularly and defining a second outer diameter, less than the first outer diameter, a sheath including a body defining a sheath lumen configured to receive the elongate medical device therethrough, and a shroud extending axially and including a first sheath aperture and a second sheath aperture, and a clip configured to transition between a first configuration and a second configuration, the clip having a first arm, including a first tab, a first plate, and a first grip, the first tab including a first keyhole aperture, a second arm, including a second tab, a second plate, and a second grip, the second tab including a second keyhole aperture, and a biasing member extending from the first arm to the second arm and configured to bias the clip towards the second configuration, the elongate medical device extending through first keyhole aperture and the second keyhole aperture, the first grip extending through the first sheath aperture, and the second grip extending through the second sheath aperture.

In some embodiments, the first arm and the second arm are spaced in a radially outward position in the second configuration relative to the first configuration. In some embodiments, the first keyhole aperture includes a first lock aperture communicating with a first unlock aperture, and the second keyhole aperture includes a second lock aperture communicating with a second unlock aperture, one or both of the first lock aperture and the second lock aperture having a first inner diameter, and one or both of the first unlock aperture and the second unlock aperture having a second inner diameter larger than the first inner diameter. In some embodiments, the first inner diameter is less than the first outer diameter and equal to or larger than the second outer diameter, and the second inner diameter is equal to or larger than the first outer diameter.

In some embodiments, the first lock aperture and the second lock aperture are axially aligned when the clip is in the second configuration, and the first unlock aperture and the second unlock aperture are axially aligned when the clip is in the first configuration. In some embodiments, the first unlock aperture and the second unlock aperture are spaced radially outward relative to a central axial position in the second configuration. In some embodiments, the first lock aperture is disposed opposite the longitudinal axis from the second lock aperture in the first configuration. In some embodiments, the sheath body is configured to engage a recess of a needle hub, the shroud extends over an outer surface of the needle hub, one or both of the first grip and the second grip engaging an outer surface of the needle hub when the clip is in the first configuration.

In some embodiments, the first grip extends through first sheath aperture to engage a first grip recess disposed in an outer surface of the needle hub, and the second grip extends through second sheath aperture to engage a second grip recess disposed in an outer surface of the needle hub. In some embodiments, one or both of the first grip and the second grip is configured to disengage the needle hub in the second configuration. In some embodiments, the first grip engages the first sheath aperture and the second grip engages the second sheath aperture in both the first configuration and the second configuration.

In some embodiments, the sheath is in a longitudinally fixed position relative the elongate medical device and a distal tip of the sheath body extends distally of a distal tip of the elongate medical device when the clip is in the second configuration. In some embodiments, the first tab, the second tab, the first grip and the second grip extend perpendicular to the longitudinal axis, and the first plate and the second plate extend parallel to the longitudinal axis. In some embodiments, the clip is formed as a monolithic piece from one of a plastic, polymer, metal, alloy, or composite. In some embodiments, the elongate medical device includes one of an obturator, needle, cannula, trocar, or a stylet.

Also disclosed is a method of engaging a safety mechanism with a tip of an elongate medical device including, withdrawing the elongate medical device proximally along a longitudinal axis, through a first keyhole aperture disposed in a first tab of a clip, transitioning the clip from a first configuration to a second configuration, the clip fixedly engaging the elongate medical device in the second configuration to prevent any longitudinal movement therebetween, the clip coupled to a sheath, and disengaging a first grip from a needle hub to disengage the sheath from the needle hub, the first grip coupled to the first tab.

In some embodiments, the clip includes a biasing member configured to bias the clip towards the second configuration. In some embodiments, the method further includes sliding the first tab perpendicular to the longitudinal axis the elongate medical device extending through a first unlock aperture of the first keyhole aperture when the clip is in a first configuration, and extending through the lock aperture when the clip is in a second configuration. In some embodiments, the method further includes engaging the first lock aperture with a notch of the elongate medical device, the inner diameter of the first lock aperture being less than a first outer diameter of the elongate medical device and larger than a second inner diameter of the notch.

In some embodiments, the method further includes fixedly engaging a sheath, coupled to the clip, relative to the elongate medical device, a distal tip of the sheath extending distally of a distal tip of the elongate medical device. In some embodiments, the first grip engages a grip recess disposed in an outer surface of the needle hub when the clip is in the first configuration. In some embodiments, the sheath includes a body defining a sheath lumen configured to receive the elongate medical device there through, and a shroud extending axially and configured to engage an outer surface of the needle hub, the first grip slidably engaged with a sheath aperture disposed in the shroud in both the first configuration and the second configuration. In some embodiments, the clip is formed as a monolithic piece from one of a plastic, polymer, metal, alloy, or composite. In some embodiments, the elongate medical device includes one of an obturator, needle, cannula, trocar, or a stylet.

Also disclosed is a method of manufacturing a safety assembly including, forming a clip from a first material, the clip having a first arm, including a first tab, a first plate, and a first grip, the first tab including a first keyhole aperture, a second arm, including a second tab, a second plate, and a second grip, the second tab including a second keyhole aperture, and a biasing member extending from the first arm to the second arm, folding the first tab and the first grip through an angle of 90 degrees relative to the first plate, folding the second tab and the second grip through an angle of 90 degrees relative to the second plate, forming a sheath from a second material, the sheath including a body defining a lumen and a shroud including a sheath aperture extending therethrough, and coupling the clip to the sheath wherein one of the first grip or the second grip extends through the sheath aperture.

In some embodiments, the method further includes elastically deforming the elongate biasing member such that the first keyhole aperture axially aligns with the second keyhole aperture. In some embodiments, the first material is a sheet of metal and the second material is a polymer.

Also disclosed is a safety mechanism including, an elongate medical device having a shaft extending along a longitudinal axis and defining a first outer diameter, the shaft including a notch extending annularly and defining a second outer diameter, less than the first outer diameter, a sheath including a body defining a lumen configured to receive the elongate medical device therethrough, and a shroud extending axially and including a sheath aperture, and a clip configured to transition between a first configuration and second configuration, the clip including, an arm, including a tab, a plate, and a grip, the tab including a keyhole aperture, and a biasing member coupled to the plate and extending annularly about an outer surface of the sheath, and configured to bias the tab towards the second configuration, the elongate medical device extending through first keyhole aperture, the grip extending through the sheath aperture.

These and other features of the concepts provided herein will become more apparent to those of skill in the art in view of the accompanying drawings and following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1:
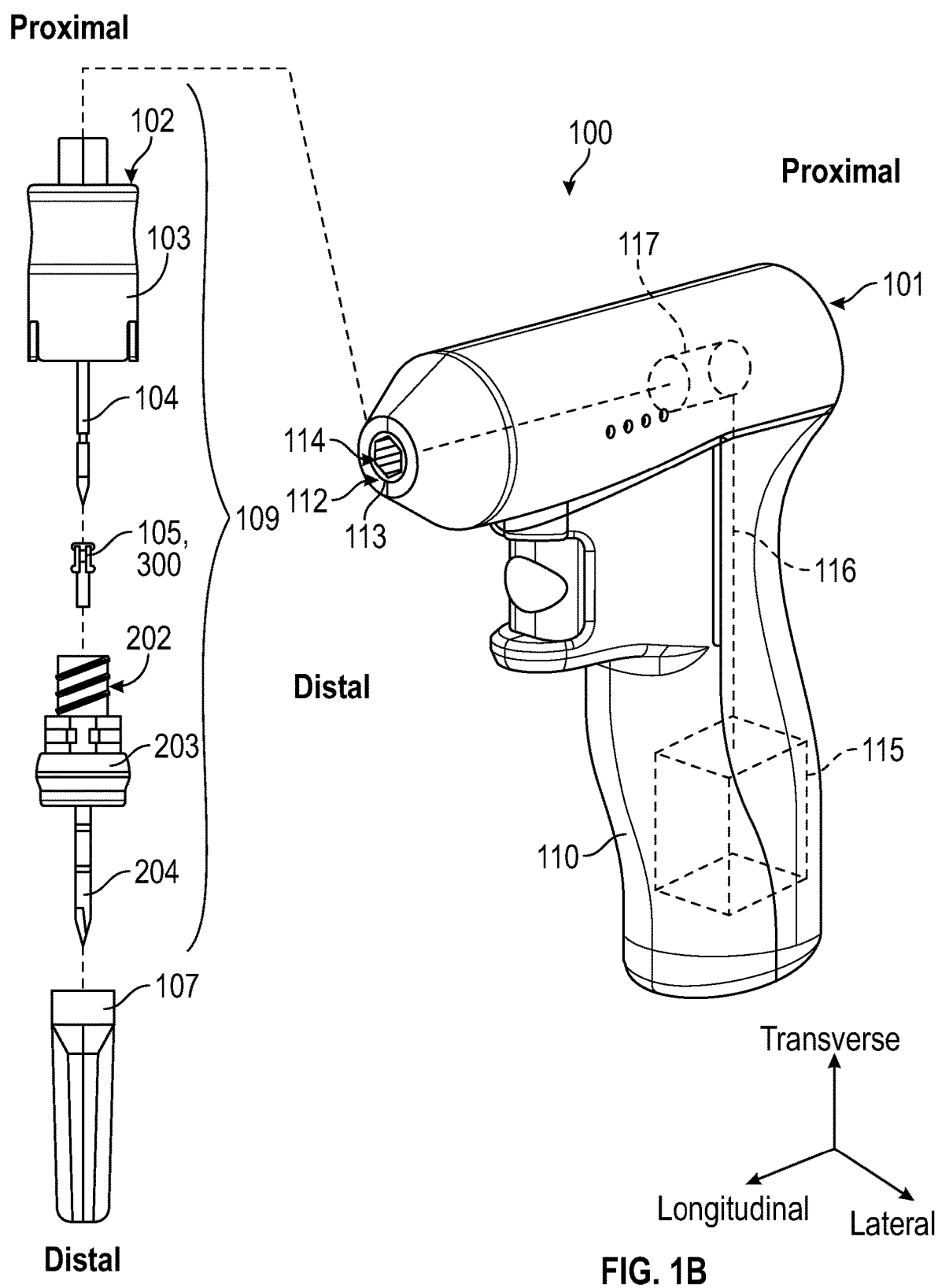
FIGS. 1A-1B illustrate an exploded view of an embodiment of an intraosseous access system, wherein an access assembly subset of the system is depicted slightly enlarged and in elevation, and an automated driver component is depicted in perspective, in accordance with some embodiments.
Figure 2:
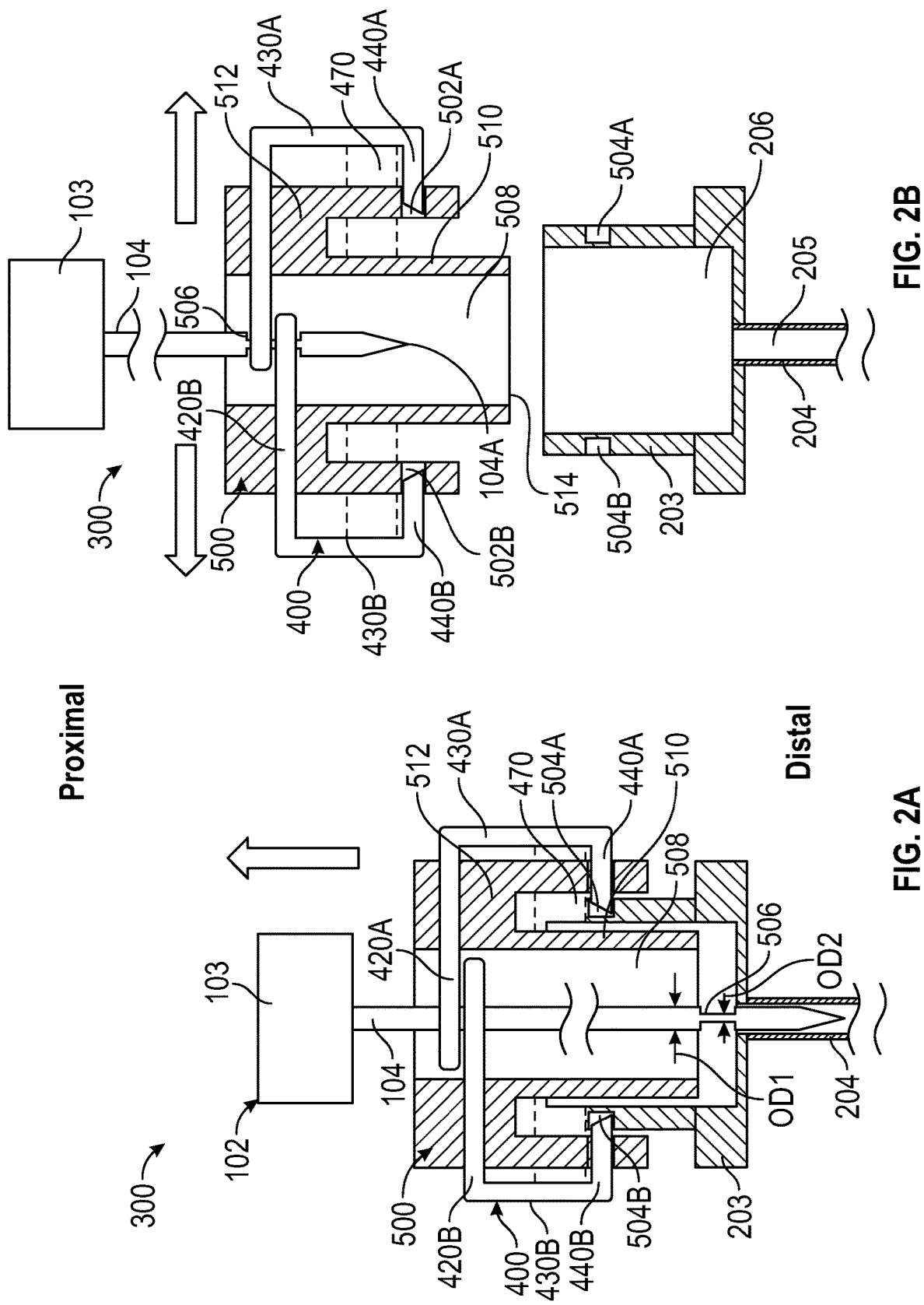
FIG. 2A illustrates a cross-section view of a safety mechanism including a clip and a sheath in a first configuration, in accordance with some embodiments.
FIG. 2B illustrates a cross-section view of a safety mechanism including a clip and a sheath in a second configuration, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a needle disclosed herein includes a portion of the needle intended to be near a clinician when the needle is used on a patient. Likewise, a "proximal length" of, for example, the needle includes a length of the needle intended to be near the clinician when the needle is used on the patient. A "proximal end" of, for example, the needle includes an end of the needle intended to be near the clinician when the needle is used on the patient. The proximal portion, the proximal-end portion, or the proximal length of the needle can include the proximal end of the needle; however, the proximal portion, the proximal-end portion, or the proximal length of the needle need not include the proximal end of the needle. That is, unless context suggests otherwise, the proximal portion, the proximal-end portion, or the proximal length of the needle is not a terminal portion or terminal length of the needle.

With respect to "distal," a "distal portion" or a "distal-end portion" of, for example, a needle disclosed herein includes a portion of the needle intended to be near or in a patient when the needle is used on the patient. Likewise, a "distal length" of, for example, the needle includes a length of the needle intended to be near or in the patient when the needle is used on the patient. A "distal end" of, for example, the needle includes an end of the needle intended to be near or in the patient when the needle is used on the patient. The distal portion, the distal-end portion, or the distal length of the needle can include the distal end of the needle; however, the distal portion, the distal-end portion, or the distal length of the needle need not include the distal end of the needle. That is, unless context suggests otherwise, the distal portion, the distal-end portion, or the distal length of the needle is not a terminal portion or terminal length of the needle.

As shown in FIG. 1, and to assist in the description of embodiments described herein, a longitudinal axis extends substantially parallel to an axial length of a needle 204 extending from the driver 101. A lateral axis extends normal to the longitudinal axis, and a transverse axis extends normal to both the longitudinal and lateral axes.

As used herein, the term "spring" is considered to include any type of spring or biasing member that may store potential mechanical energy. Exemplary biasing members can include compression springs, extension springs, torsion springs, constant force springs, flat spring, flexible members, rubber rings, rubber band, leaf spring, V-spring, cantilever spring, volute spring, Belleville spring, gas spring, gravity-propelled biasing members, combinations thereof or the like, and are considered to fall within the scope of the present invention.

Unless defined otherwise, all technical and scientific terms used herein have the same meaning as commonly understood by those of ordinary skill in the art. Although the exemplary embodiments disclosed herein are described with respect to intraosseous (IO) access devices, systems, and methods thereof, it will be appreciated that embodiments disclosed herein can be used with various systems that require capturing a sharp tip of an elongate device to mitigate accidental stick injuries, without limitation.

FIGS. 1A-1B show an exemplary environment of use for a safety mechanism 300, as described herein. FIGS. 1A-1B show an exploded view of an exemplary intraosseous access system ("system") 100, with some components thereof shown in elevation (FIG. 1A) and other components shown in perspective (FIG. 1B). In an embodiment, the intraosseous access system 100 can be used to penetrate the skin tissues and underlying hard bone ("bone cortex") for intraosseous access, such as, for example to access the marrow of the bone and/or a vasculature of the patient via a pathway through an interior of the bone ("medullary cavity").

In an embodiment, the system 100 includes a driver 101 and an access assembly 109. The driver 101 can be used to rotate the access assembly 109 and "drill" a needle 204 into the bone of a patient. In embodiments, the driver 101 can be automated or manual. As shown, the driver 101 is an automated driver 101. For example, the automated driver 101 can be a drill that achieves high rotational speeds. In an embodiment, the intraosseous access system 100 can further include an obturator assembly 102, a safety mechanism or shield 105, and a needle assembly 202, which may be referred to, collectively, as the access assembly 109. The needle assembly 202 can include an access needle ("needle") 204 supported by a needle hub 203, as described in more detail herein. In an embodiment, the obturator assembly 102 includes an obturator 104. However, in some embodiments, the obturator 104 may be replaced with a different elongated medical instrument. As used herein, the term "elongated medical instrument" is a broad term used in its ordinary sense that includes, for example, such devices as needles, cannulas, trocars, obturators, stylets, and the like. Accordingly, the obturator assembly 102 may be referred to more generally as an elongated medical device assembly. In like manner, the obturator 104 may be referred to more generally as an elongated medical device.

In an embodiment, the obturator assembly 102 includes a coupling hub 103 that is attached to the obturator 104 in any suitable manner (e.g., one or more adhesives or overmolding). The coupling hub 103 can be configured to interface with the driver 101, as further discussed below. The coupling hub 103 may alternatively be referred to as an obturator hub 103 or, more generally, as an elongated instrument hub 103. In an embodiment, the safety mechanism 105 is configured to couple with the obturator 104 to prevent accidental needle stick injuries when the obturator is removed after placement of the needle 204, as described in more detail herein.

In an embodiment, the needle assembly 202 includes a needle 204. However, in some embodiments, the needle 204 may be replaced with a different instrument, such as, for example, a cannula, a tube, or a sheath, and/or may be referred to by a different name, such as one or more of the foregoing examples. Accordingly, the needle assembly 202 may be referred to more generally as a cannula assembly or as a tube assembly. In like manner, the needle 204 may be referred to more generally as a cannula.

In an embodiment, the needle assembly 202 includes a needle hub 203 that is attached to the needle 204 in any suitable manner. The needle hub 203 can be configured to couple with the obturator hub 103 and may thereby be coupled with the driver 101. The needle hub 203 may alternatively be referred to as a cannula hub 203. In an embodiment, a cap 107 may be provided to cover at least a distal portion of the needle 204 and the obturator 104 prior to use of the access assembly 109. For example, in an embodiment, a proximal end of the cap 107 can be coupled to the obturator hub 103.

With continued reference to FIG. 1B, the driver 101 may take any suitable form. The driver 101 may include a handle 110 that may be gripped by a single hand of a user. In an embodiment, the driver 101 further includes a coupling interface 112, which is formed as a socket 113 that defines a cavity 114. The coupling interface 112 can be configured to couple with the obturator hub 103. In an embodiment, the socket 113 includes sidewalls that substantially define a hexagonal cavity into which a hexagonal protrusion of the obturator hub 103 can be received. Other suitable connection interfaces are also contemplated.

The driver 101 can include an energy source 115 of any suitable variety that is configured to energize the rotational movement of the coupling interface 112. For example, in some embodiments, the energy source 115 may comprise one or more batteries that provide electrical power for the driver 101. In some embodiments, the energy source 115 can comprise one or more springs (e.g., a coiled spring, flat spring, or the like) or other biasing member that may store potential mechanical energy that may be released upon actuation of the driver 101.

The energy source 115 may be coupled with the coupling interface 112 in any suitable manner. For example, in an embodiment, the driver 101 includes an electrical, mechanical, or electromechanical coupling 116 to a gear assembly 117. In some embodiments, the coupling 116 may include an electrical motor that generates mechanical movement from electrical energy provided by an electrical energy source 115. In other embodiments, the coupling 116 may include a mechanical linkage to the gear assembly 117. The driver 101 can include a mechanical coupling of any suitable variety to couple the gear assembly 117 with the coupling interface 112. In other embodiments, the gear assembly 117 may be omitted.

Further details and embodiments of the intraosseous access system 100 can be found in WO 2018/075694, WO 2018/165334, WO 2018/165339, and U.S. Pat. No. 10,893,887, each of which are incorporated by reference in their entirety into this application.

FIGS. 2A-5D illustrate various details of an embodiment of a safety mechanism 300. The safety mechanism 300 can be used with an intraossesous access system 100, as described herein, for example, the safety mechanism 300 can be used in place of the safety shield 105. However, it will be appreciated that embodiments of the safety mechanism 300 can be used with various needles, cannulas, trocars, stylets, obturators, or similar sharpened medical devices without limitation, and can be configured to prevent accidental needle-stick injuries.

As shown in FIGS. 2A-2B, in an embodiment, the safety mechanism 300 can generally include a clip 400 and a sheath 500. A portion of the clip 400 can slidably engage the sheath 500 and transition between a first, or unlocked, configuration (FIG. 2A) and a second, or locked, configuration (FIG. 2B). In the first configuration, as shown in FIG. 2A, the clip 400 can slidably engage a shaft of the obturator 104 along a longitudinal axis thereof. Further, the clip 400 can also selectively engage the needle hub 203 and secure the sheath 500 thereto, preventing any relative longitudinal movement between the sheath 500 and the needle hub 203.

As the obturator 104 is withdrawn proximally from the needle 204 and slides relative to the safety mechanism 300, an annular notch ("notch") 506 aligns with a portion of the clip 400, allowing the clip 400 to transition from the first configuration (FIG. 2A) to the second configuration (FIG. 2B). In the second configuration, the clip 400 is locked to the obturator 104, preventing any relative longitudinal movement between the obturator 104 and safety mechanism 300. Further, the clip 400 disengages the needle hub 203 allowing the obturator 104, clip 400, and sheath 500 assembly to separate from the needle hub 203.

Advantageously, the clip 400 maintains the sheath 500 in a longitudinally fixed position relative to the tip of the obturator 104 preventing accidental stick injuries. Further, the safety mechanism 300 provides a simplified manufacturing process, and associated cost savings. Advantageously, the clip 400 requires only a relatively small surface area to contact the obturator 104, reducing friction or "drag" therebetween as the obturator 104 is slid proximally. Further the edges of the clip 400 can be smoothed and/or beveled to further reduce the friction between the clip 400 and the obturator 104. As such, less force is required to remove the obturator 104 from the needle 204 and can prevent the obturator 104 from becoming prematurely detached from the driver 101. Advantageously, the engagement between the clip 400, the sheath 500, and the needle hub 203 in the first configuration (FIG. 2A) requires much higher override forces providing a much more robust interface, mitigating accidental failure of the safety mechanism 300.

Figure 3:
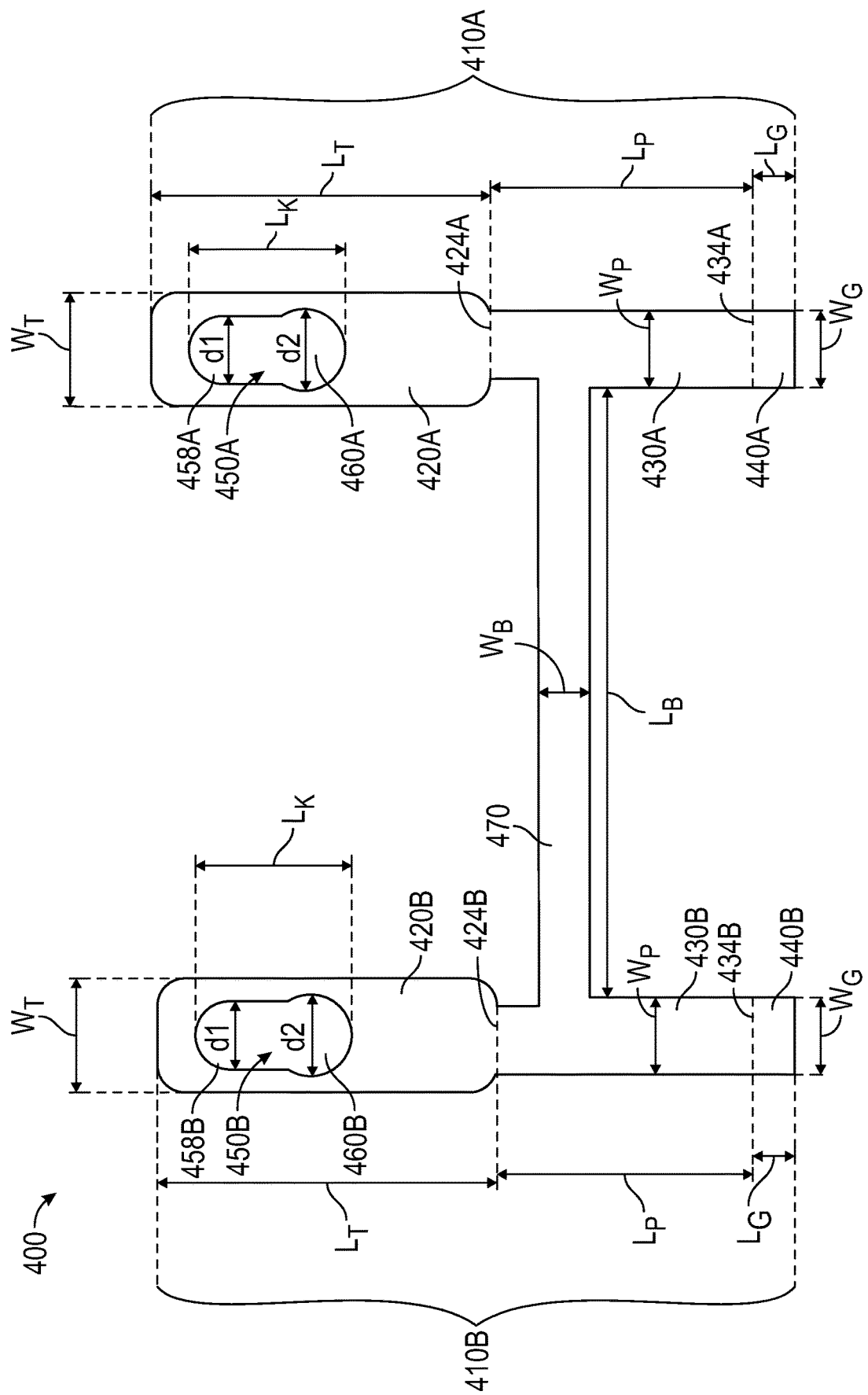
FIG. 3 illustrates a clip of the safety mechanism of FIGS. 2A-2B in an unfolded configuration, in accordance with some embodiments.
Figure 4B:
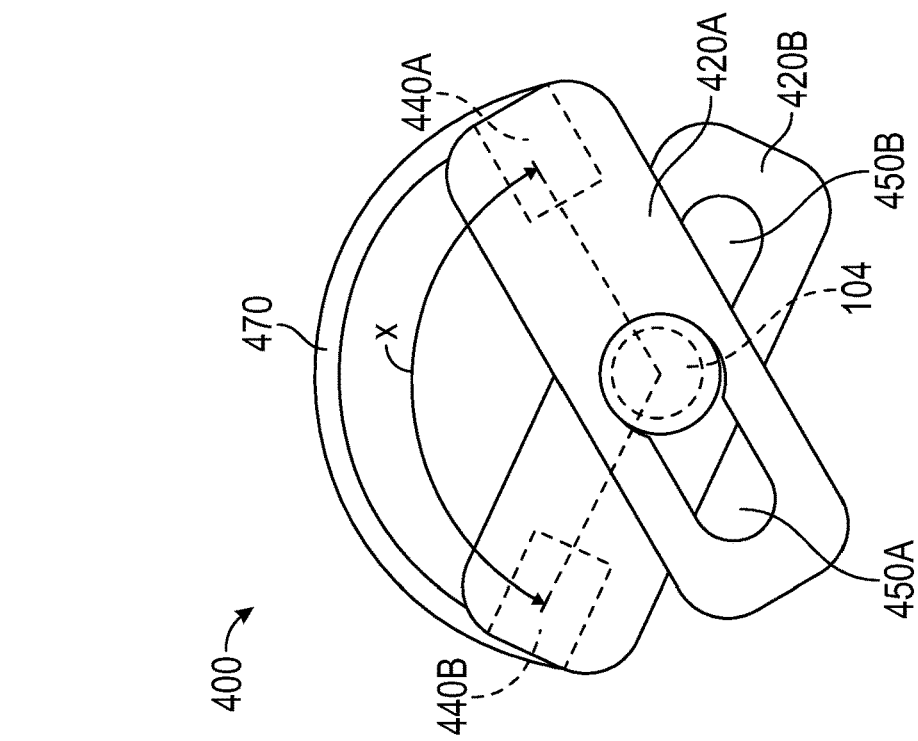
FIG. 4B illustrates a plan view of the clip of FIG. 3 in a folded configuration, in accordance with some embodiments.
Figure 4A:
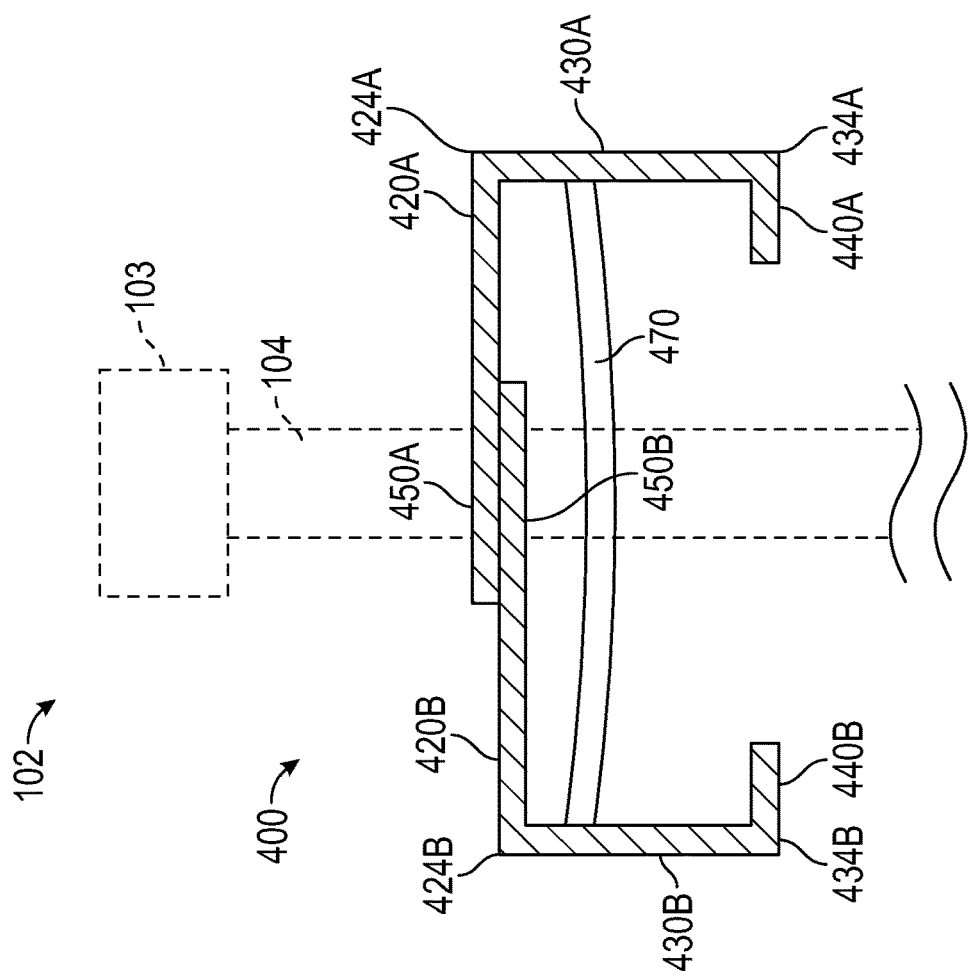
FIG. 4A illustrates a side view of the clip of FIG. 3 in a folded configuration, in accordance with some embodiments.

FIGS. 3-4B show further details of the clip 400 of the safety mechanism 300. FIG. 3 shows the clip 400 in an unfolded configuration. FIGS. 4A-4B show the clip 400 in a folded configuration. In an embodiment, the clip 400 can be formed as a single monolithic piece. For example, the safety mechanism can be stamped from a sheet of metal, polymer, plastic, composite, or the like and shaped into the folded configuration (FIGS. 4A-4B). Optionally, a portion of the clip 400 can be heated to facilitate folding of the clip 400. Advantageously, the clip 400, formed as such, simplifies the manufacturing process and reduces associated costs and complexity. FIG. 4A shows a side view of the clip 400 in a folded configuration. FIG. 4B shows a plan view of the clip 400 in a folded configuration.

The clip 400 generally includes a first arm 410A and a second arm 410B and a biasing member 470 extending therebetween. In an embodiment, each arm 410 can include a tab 420 (e.g. a first tab 420A and a second tab 420B), a plate 430 (e.g. a first plate 430A and a second plate 430B), and a grip 440 (e.g. a first grip 440A and a second grip 440B). In an embodiment, the biasing member 470 can be a flat spring, a leaf spring, or the like, and can extend between the first plate 430A and the second plate 430B. In an embodiment, the biasing member 470 can extend between the first tab 420A and the second tab 420B.

As shown in FIG. 3, each arm 420 can include a tab foldline 424, disposed between the tab 420 and the plate 430, and a grip foldline 434 disposed between the plate 430 and the grip 440. In an embodiment, the tab foldline 424 or the grip foldline 434 can include a score line, groove, perforation, laser cut line or similar line of weakness to facilitate folding of the arm 410 therealong, as described in more detail herein.

In an embodiment, each tab 420 can define a tab length ($L_T$) and a tab width ($W_T$). Each plate 430 can define a plate length ($L_P$) and a plate width ($W_P$). Each grip 440 can define a grip length ($L_G$) and a grip width ($W_G$). In an embodiment, the tab length ($L_T$) can be equal to, or greater than, the tab width ($W_T$). In an embodiment, the tab length ($L_T$) can be equal to, or greater than the plate length ($L_P$). In an embodiment, the tab width ($W_T$) can be equal to, or greater than the plate width ($W_P$).

In an embodiment, the plate length ($L_P$) can be equal to or greater than the plate width ($W_P$). In an embodiment, the plate length ($L_P$) can be equal to, or greater than the grip length ($L_G$). In an embodiment, the grip length ($L_G$) can be equal to, less than, or greater than the grip width ($W_G$). In an embodiment, the grip width ($W_G$) can be substantially equal to the plate width ($W_P$). In an embodiment, the grip width ($W_G$) can be greater than, or less than the plate width ($W_P$).

In some embodiments, the tab length ($L_T$) of the first tab 420A can be equal to the tab length ($L_T$) of the second tab 420B. In some embodiments, the tab length ($L_T$) of the first tab 420A can be different from the tab length ($L_T$) of the second tab 420B. In some embodiments, the plate length ($L_P$) of the first plate 430A can be equal to the plate length ($L_P$) of the second plate 430B. In some embodiments, the plate length ($L_P$) of the first plate 430A can be different from the plate length ($L_P$) of the second plate 430B. In some embodiments, the grip length ($L_G$) of the first grip 440A can be equal to the grip length ($L_G$) of the second grip 440B. In some embodiments, the grip length ($L_G$) of the first grip 440A can be different from the grip length ($L_G$) of the second grip 440B.

In an embodiment, the tab 420 can further include a keyhole aperture 450 substantially defining a "keyhole" shape and defining a keyhole aperture length ($L_K$). For example, the first tab 420A can include a first keyhole aperture 450A, and the second tab 420B can include a second keyhole aperture 450B. Each keyhole aperture 450 can include a lock aperture 458 communicating with an unlock aperture 460. The lock aperture 458 can define a first inner diameter (d1), and the unlock aperture 460 can define a second inner diameter (d2), larger than the first diameter (d1). In an embodiment, the diameter (d2) of the unlock aperture 460 is equal to or greater than an outer diameter of the obturator 104.

In an embodiment, the diameter (d1) of the lock aperture 458 is less than an outer diameter of the obturator 104. In an embodiment, the diameter (d1) of the lock aperture 458 is equal to or greater than the diameter of the notch 506. To note, the outer diameter (OD2) of the notch 506 is less than an outer diameter (OD1) of the obturator 104. In an embodiment, the keyhole aperture length ($L_K$) can be equal to or greater than the first diameter (d1) and the second diameter (d2) combined.

In an embodiment, the biasing member 470 can extend from the first arm 410A to the second arm 410B to define a biasing member length ($L_B$), and can define a biasing member width ($W_B$) extending perpendicular thereto. In an embodiment, the biasing member length ($L_B$) is greater than the biasing member width ($W_B$). In an embodiment, as shown in FIG. 4B, the biasing member length ($L_B$) can extend through less than 360° of the circumference of the sheath 500, e.g. through an arc distance (x).

In an embodiment, the biasing member 470 can couple to the first arm 410A or the second arm 410B at any position therealong. In an embodiment, the biasing member 470 can couple to the first plate 430A or the second plate 430B at any position therealong. In an embodiment, an axis of the elongate biasing member 470 can extend perpendicular to an axis of the first arm 410A or the second arm 410B and can couple to the first arm 410A and the second arm 410B at a similar position therealong. In an embodiment, an axis of the elongate biasing member 470 can extend at an angle relative to an axis of the first plate arm 410A or the second arm 410B and can couple to the first arm 410A and the second arm 410B at different positions.

In an embodiment, the keyhole apertures 450 can be oriented on the respective tabs 420 in the same direction or in different directions. For example, the first keyhole aperture 450A can be oriented with the first unlock 460A aperture disposed closer to the first plate 430A and the second keyhole aperture 450B can be oriented with the second lock aperture 458B disposed closer to the second plate 430B. In other embodiments, the first keyhole aperture 450A can be oriented with the first lock aperture 458A disposed closer to the first plate 430A and the second keyhole aperture 450B can be oriented with the second unlock aperture 460B disposed closer to the second plate 430B. These and other orientations of keyhole apertures are considered to fall within the scope of the present invention.

FIG. 4A shows a side view of the clip 400 in the folded configuration. FIG. 4B shows a plan view of the clip 400 in the folded configuration. In an embodiment, to transition the clip 400 from the unfolded configuration (FIG. 3) to the folded configuration (FIGS. 4A, 4B), the first tab 420A can be folded, relative to the first plate 430A, along the first plate fold line 424A, through an angle of substantially 90°. The second tab 420B can be folded, relative to the second plate 430B, along the second plate fold line 424B, through an angle of substantially 90°. The first grip 440A can be folded, relative to the first plate 430A, along the first grip fold line 434A through an angle of substantially 90°. The first grip 440A can extend substantially parallel to the first tab 420A. The second grip 420B can be folded, relative to the second plate 430B, along the second grip fold line 434B, through an angle of substantially 90°. The second grip 440B can extend substantially parallel to the second tab 420B.

The elongate biasing member 470 can be elastically deformed such that a portion of first keyhole aperture 450A overlaps a portion of the second keyhole aperture 450B and aligns with a central longitudinal axis, substantially defined by obturator 104. As such, in the folded configuration, the first tab 420A and the second tab 420B extend radially inward. Similarly, the first grip 440A and the second grip 440B extend radially inward, relative to a central longitudinal axis of the obturator 104. The first plate 430A and the second plate 430B can extend substantially parallel to the central longitudinal axis.

In the folded configuration, in an embodiment, the first tab 420A can be positioned above the second tab 420B. In other embodiments, the second tab 420B can be positioned above the first tab 420A. In some embodiments, the elongated biasing member 470 can be elastically deformed to define an arcuate shape. The biasing member 470 can extend along a portion of the circumference of the sheath 500. As shown in FIG. 4B, in an embodiment, the elongate biasing member 470, in the elastically deformed configuration, extends through an arc distance (x) of between 5° and 360°. In an embodiment, the elongate biasing member 470 in the elastically deformed configuration extends through an arc distance of between 100° and 200°.

In an embodiment, the clip 400 may be formed by 3D printed, injection molded, or the like, in the folded configuration, or formed in the unfolded configuration and then folded to the folded configuration, as described herein. In an embodiment, the clip 400 can be formed from two or more pieces joined together by welding, bonding, adhesive, or the like in the folded configuration, or formed in the unfolded configuration and then folded to the folded configuration, as described herein.

Figure 5A:
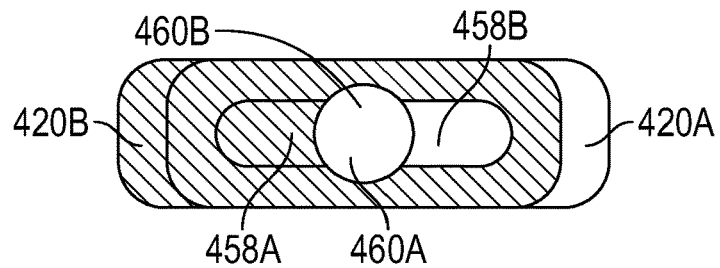
FIG. 5A illustrates a plan view of a first tab and a second tab of a clip in a first configuration, in accordance with some embodiments.
Figure 5B:
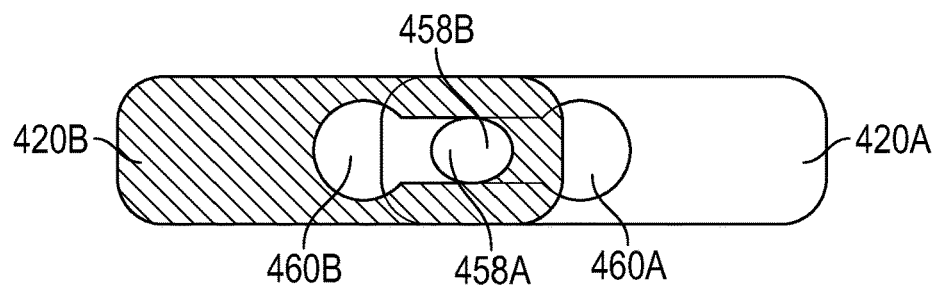
FIG. 5B illustrates a plan view of a first tab and a second tab of a clip in a second configuration, in accordance with some embodiments.
Figures 5C, 5D:
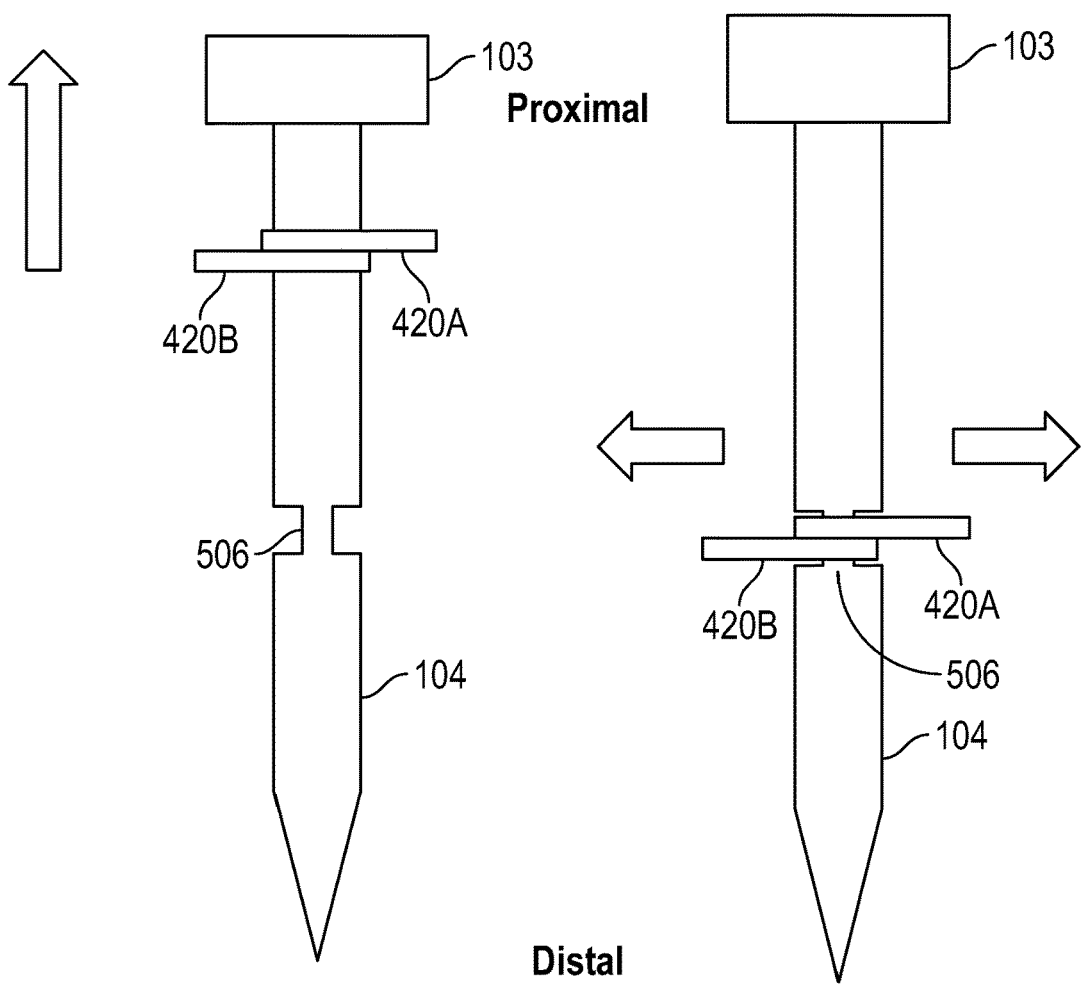
FIG. 5C illustrates a side view of a clip and an obturator in a first configuration, in accordance with some embodiments.
FIG. 5D illustrates a side view of a clip and an obturator in a second configuration, in accordance with some embodiments.

FIGS. 5A-5D show an exemplary method of use for the clip 400. FIG. 5A shows a plan view of the first tab 420A and the second tab 420B in the first, or unlocked, configuration. FIG. 5B shows a plan view of the first tab 420A and the second tab 420B in the second, or locked, configuration. FIG. 5C shows a side view of the obturator 104 and the first tab 420A and the second tab 420B in the first configuration. FIG. 5D shows a side view of the obturator 104 and the first tab 420A and the second tab 420B in the second configuration. To note, the biasing member 470 is not shown for clarity. Further, the first tab 420A is shown as ghosted to show the relative position of the second tab 420B disposed there below. The elastic properties of the elongate biasing member 470 biases the first tab 420A and the second tab 420B towards the second configuration (FIG. 5B).

In the first configuration, as shown in FIGS. 5A and 5C, the first unlock aperture 460A aligns with the second unlock aperture 460B to define an opening sufficient to allow an outer diameter of the obturator 104 to pass therethrough. In some embodiments, the first configuration with the first unlock aperture 460A and the second unlock aperture 460B aligning is the natural higher energy state of the clip 400. As illustrated in FIGS. 5B and 5D, as the obturator 104 is withdrawn proximally from the needle 204, the notch 506 of the obturator 104 longitudinally aligns with the first keyhole aperture 450A and the second keyhole aperture 450B. Since the outer diameter (OD2) of the notch 506 is less than the diameter (d1) of the lock aperture 458, the notch 506 allows the biasing member 470 to transition the clip 400 from the first configuration to the second configuration. In the second configuration, the first tab 420A and the second tab 420B are displaced radially outward relative to a central longitudinal axis.

In some embodiments, the second configuration with the first lock aperture 458A and the second lock aperture 458B aligning with the central longitudinal axis, is the natural lower energy state of the clip 400. To note, as shown in FIGS. 5B and 5D, the first tab 420A, with the first grip 440A coupled thereto, and the second tab 420B, with the second grip 440B coupled thereto, are disposed radially outward in the second configuration, relative to the first configuration.

Advantageously, the clip 400 in the second configuration mitigates failure of the safety mechanism 300. The biasing member 470 urges the first tab 420A and the second tab 420B to engage the notch 506 and prevent vertical movement of the obturator 104 relative to the clip 400. As such, to transition the clip 300 from the second configuration to the first configuration and allow relative vertical movement of the obturator 104, the notch 506 must be longitudinally aligned with the keyhole apertures 450A. The first arm 410A and the second arm 410B must be urged radially inward, perpendicular to the longitudinal axis, and with sufficient force to overcome the force of the biasing member 470. The first unlock aperture 460A and the second unlock aperture 460B must be displaced radially inward and aligned with the central longitudinal axis. Advantageously, applying an axial force alone cannot cause the clip 400 to accidentally transition from the second configuration to the first configuration, causing accidental disengagement of the sheath 500 from the tip of the obturator 104.

With continued reference to FIGS. 2A-2B, the safety mechanism 300, including the clip 400 and the sheath 500 can selectively engage the needle hub 203. FIG. 2A shows the safety mechanism 300 in the first configuration, whereby the obturator 104 is slidably engaged with the clip 400. FIG. 2B shows the clip 400 in the second configuration whereby the sheath 500 is in a fixed longitudinal position relative to a distal tip of the obturator 104. With the safety mechanism 300 in the second configuration, a distal edge 514 of the sheath 500 extends distally of the distal tip 104A of the obturator 104 to mitigate accidental stick injuries.

The needle hub 203 can support the needle 204 defining a needle lumen 205. The needle hub 203 can define a hub recess 206 communicating with the needle lumen 205. The sheath 500 can include a body 510, defining a sheath lumen 508, and a shroud 512 extending axially therefrom. A portion of the sheath body 510 can be configured to extend into the needle hub recess 206 and can engage an inner surface thereof. In an embodiment, the sheath 500, or portion thereof (e.g. the body 510 or the shroud 512), can engage the needle hub 203 in an interference fit, snap-fit engagement, luer lock engagement, threaded engagement, combinations thereof, or the like.

The sheath lumen 508 can be configured to receive the obturator 104 extending therethrough. The sheath 500 can further include a shroud 512 extending axially. The sheath 512 can extend over an outer surface of the needle hub 203 when the sheath body 510 is engaged with the needle hub recess 206. In an embodiment, an inner surface of the shroud 512 can slidably engage an outer surface of the needle hub 203. In an embodiment, the sheath shroud 512 can include one or more sheath apertures 502, e.g. a first aperture 502A and a second aperture 502B, extending through the shroud 512, perpendicular to the longitudinal axis. In some embodiments, the one or more apertures 502 can communicate with a channel (not shown) extending annularly around the outer circumference of the sheath shroud 512.

In the first configuration (FIG. 2A), the first arm 410A and the second arm 410B are disposed radially inward relative to each other and the obturator 104 can slide longitudinally relative to the safety mechanism 300. The grip 440 of the arm 410 can extend through the aperture 502 and engage an outer surface of the needle hub 203. In an embodiment, the grip 440 can engage a grip recess 504 disposed in an outer surface of the needle hub 203. For example, as shown in FIG. 2A with the sheath 500 engaged with the needle hub 203, a first grip 440A can extend through the first sheath aperture 502A and engage a first grip recess 504A. A second grip 440B can extend through the second sheath aperture 502B and engage a second grip recess 504B. As such, the clip 400 can secure the sheath 500 to the needle hub 203 and can prevent disengagement therefrom when an axial force is applied.

Advantageously, the sheer strength of the grips 440 mitigates premature disengagement of the safety mechanism 300 from the needle hub 203 as the obturator 104 is withdrawn proximally. Worded differently, the sheer forces of the grip 440 interacting with the grip recess 504 are greater than the frictional forces of the keyhole apertures 450 interacting with the obturator 104. As such, the grip 440 prevents the sheath 500 from disengaging the needle hub 203.

As shown in FIG. 2B, as the obturator 104 is withdrawn proximally, the notch 506 longitudinally aligns with the keyhole apertures 450A, 450B. The smaller outer diameter of the notch 506 can allow the clip 400 to transition from the first configuration to the second configuration. In the second configuration the first arm 410A and the second arm 410B can be displaced radially outward relative to each other. As such the grips 440A, 440B are also displaced radially outward and disengage grip recesses 504A, 504B of the needle hub 203. As such, the sheath 500 can disengage the needle hub 203. In an embodiment, the length ($L_G$) of the grips 440A, 440B, are sufficient to allow the grips 440A, 440B to remain engaged with the sheath apertures 502A, 502B respectively, so that the clip 400 remains engaged with the sheath 500 in both the first configuration and the second configuration. The obturator 104, with the safety mechanism 300 engaged there can be removed. As noted, the distal tip 514 of the sheath 500 in the second configuration extends distally of the distal tip 104A of the obturator 104 to prevent accidental needle stick injuries.

Advantageously, embodiments of the safety mechanism 300, as described herein, provide a simplified manufacturing process and reduce associated costs. The clip 400 can be stamped from a single sheet of material and folded into position. The sheath 500 and needle hub 203 can be molded in a single process that negates any secondary machining.

Figure 6A:
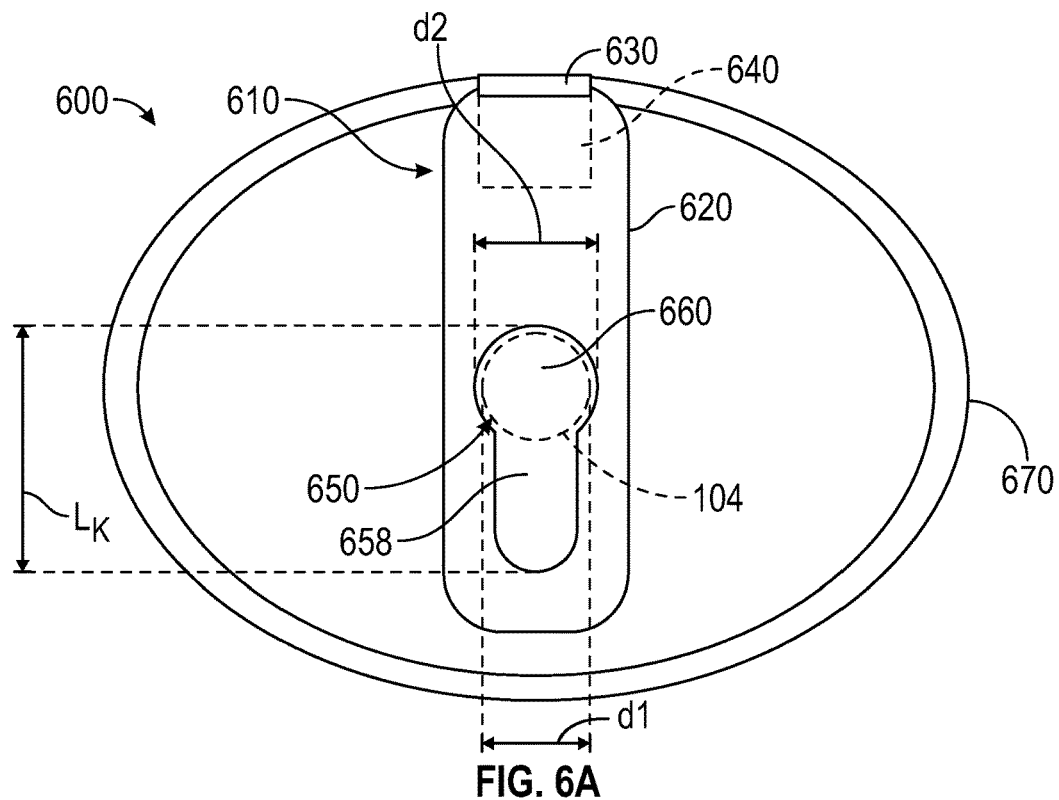
FIG. 6A illustrates a clip having a single tab in a first configuration, in accordance with some embodiments.
Figure 6B:
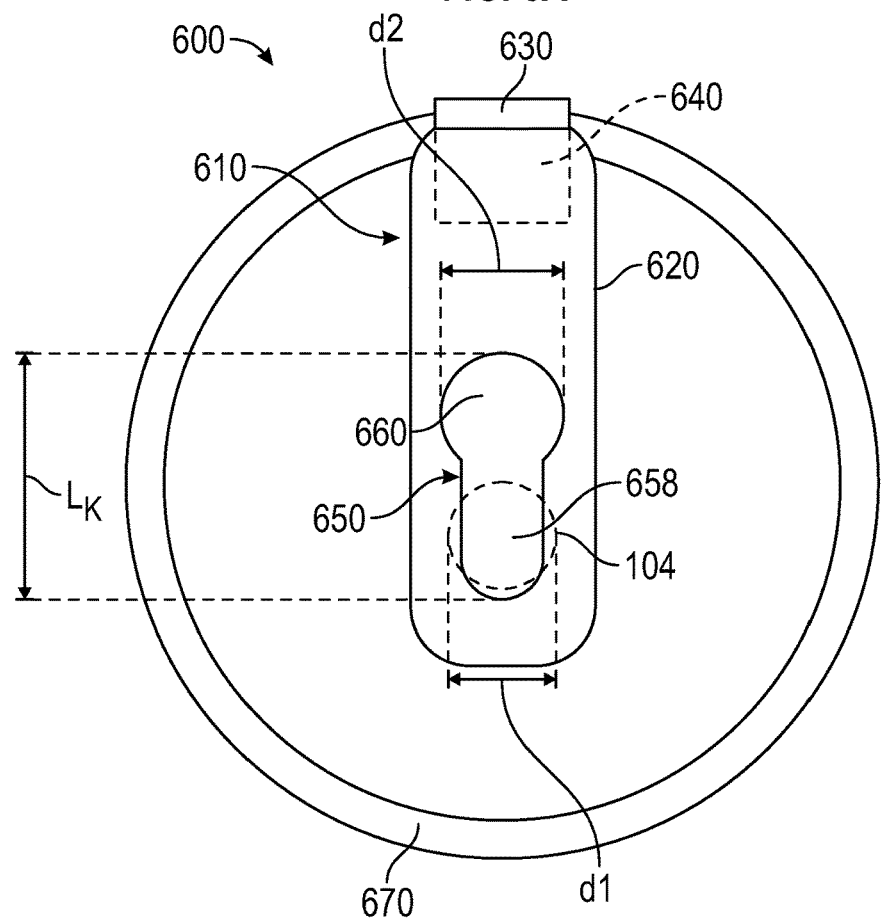
FIG. 6B illustrates a clip having a single tab in a second configuration, in accordance with some embodiments.

FIGS. 6A-6B show an embodiment of a clip 600 including a single tab 620 configured to be used with the sheath 500 of the safety mechanism 300. FIG. 6A shows a plan view of the clip 600 in the first configuration. FIG. 6B shows a plan view of the clip 600 in the second configuration. The clip 600 can include an arm 610 and a biasing member 670 coupled thereto. In an embodiment, the arm 610 can include a tab 620, a plate 630 and a grip 640. The tab 620 includes a keyhole aperture 650 defining a keyhole aperture length ($L_K$) and having a lock aperture 658 communicating with an unlock aperture 660.

In an embodiment, the biasing member 670 extending annularly about the sheath 500. For example, the biasing member 670 can be coupled to the plate 630 and extend through 360° around the entire outer circumference of the sheath 500. In an embodiment, the biasing member 670 can extend through less than 360° e.g. around at least half of the outer circumference of the sheath 500. In an embodiment, a portion of the biasing member 670, e.g. a portion disposed opposite the plate 630 can be coupled with sheath 500. In an embodiment, the elongate biasing member 670 can elastically deform between a first configuration (FIG. 6A), and a second configuration (FIG. 6B). The biasing member 670 biases the clip 600 towards a second configuration (FIG. 6B). In the first configuration, the grip 640 can engage a sheath aperture 502 and a grip recess 504 to engage the sheath 500 with the needle hub 203, as described herein. In the second configuration, the tab 620 engages the notch 506 of the obturator 104 to lock the sheath 500 relative to the obturator tip 104A, the radially outward movement of the plate 630 disengages the grip 640 from the grip recess 504 allowing the safety mechanism 300 to disengage the needle hub 203, as described herein.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A safety mechanism, comprising:
    an elongate medical device having a shaft extending along a longitudinal axis and defining a first outer diameter, the shaft including a notch extending annularly and defining a second outer diameter, less than the first outer diameter;
    a sheath including a body defining a sheath lumen configured to receive the elongate medical device therethrough, and a shroud extending axially and including a first sheath aperture and a second sheath aperture;
    a needle hub defining a recess, the body of the sheath configured to engage the recess of the needle hub, the shroud configured to extend over an outer surface of the needle hub; and
    a clip configured to transition between a first configuration and a second configuration, the clip comprising:
        a first arm, including a first tab, a first plate, and a first grip, the first tab including a first keyhole aperture;
        a second arm, including a second tab, a second plate, and a second grip, the second tab including a second keyhole aperture; and
        a biasing member extending from the first arm to the second arm and configured to bias the clip towards the second configuration, the elongate medical device extending through the first keyhole aperture and the second keyhole aperture, the first grip extending through the first sheath aperture, and the second grip extending through the second sheath aperture, wherein one or both of the first grip and the second grip engage the outer surface of the needle hub when the clip is in the first configuration.

2. The safety mechanism according to claim 1, wherein the first arm and the second arm are spaced in a radially outward position in the second configuration relative to the first configuration.

3. The safety mechanism according to claim 1, wherein the first keyhole aperture includes a first lock aperture communicating with a first unlock aperture, and the second keyhole aperture includes a second lock aperture communicating with a second unlock aperture, one or both of the first lock aperture and the second lock aperture having a first inner diameter, and one or both of the first unlock aperture and the second unlock aperture having a second inner diameter larger than the first inner diameter.

4. The safety mechanism according to claim 3, wherein the first inner diameter is less than the first outer diameter and equal to or larger than the second outer diameter, and the second inner diameter is equal to or larger than the first outer diameter.

5. The safety mechanism according to claim 3, wherein the first lock aperture and the second lock aperture are axially aligned when the clip is in the second configuration, and the first unlock aperture and the second unlock aperture are axially aligned when the clip is in the first configuration.

6. The safety mechanism according to claim 3, wherein the first unlock aperture and the second unlock aperture are spaced radially outward relative to a central axial position in the second configuration.

7. The safety mechanism according to claim 3, wherein the first lock aperture is disposed opposite the longitudinal axis from the second lock aperture in the first configuration.

8. The safety mechanism according to claim 1, wherein the first grip extends through the first sheath aperture to engage a first grip recess disposed in the outer surface of the needle hub, and the second grip extends through the second sheath aperture to engage a second grip recess disposed in the outer surface of the needle hub.

9. The safety mechanism according to claim 1, wherein one or both of the first grip and the second grip is configured to disengage the needle hub in the second configuration.

10. The safety mechanism according to claim 1, wherein the first grip engages the first sheath aperture and the second grip engages the second sheath aperture in both the first configuration and the second configuration.

11. The safety mechanism according to claim 1, wherein the sheath is in a longitudinally fixed position relative the elongate medical device and a distal tip of the body of the sheath extends distally of a distal tip of the elongate medical device when the clip is in the second configuration.

12. The safety mechanism according to claim 1, wherein the first tab, the second tab, the first grip, and the second grip extend perpendicular to the longitudinal axis, and the first plate and the second plate extend parallel to the longitudinal axis.

13. The safety mechanism according to claim 1, wherein the clip is formed as a monolithic piece from one of a plastic, polymer, metal, alloy, or composite.

14. The safety mechanism according to claim 1, wherein the elongate medical device includes one of an obturator, needle, cannula, trocar, or a stylet.

15. A method of engaging a safety mechanism with a tip of an elongate medical device, comprising:
- withdrawing the elongate medical device proximally along a longitudinal axis, through a first keyhole aperture disposed in a first tab of a clip;
- transitioning the clip from a first configuration to a second configuration, the clip fixedly engaging the elongate medical device in the second configuration to prevent any longitudinal movement therebetween, the clip coupled to a sheath; and
- disengaging a first grip from a needle hub to disengage the sheath from the needle hub, the first grip coupled to the first tab, wherein the sheath includes a body defining a sheath lumen configured to receive the elongate medical device there through, and a shroud extending axially and configured to engage an outer surface of the needle hub, the first grip slidably engaged with a sheath aperture disposed in the shroud in both the first configuration and the second configuration.

16. The method according to claim 15, wherein the clip includes a biasing member configured to bias the clip towards the second configuration.

17. The method according to claim 15, further including sliding the first tab perpendicular to the longitudinal axis, the elongate medical device extending through a first unlock aperture of the first keyhole aperture when the clip is in the first configuration, and extending through a first lock aperture when the clip is in the second configuration.

18. The method according to claim 17, further including engaging the first lock aperture with a notch of the elongate medical device, an inner diameter of the first lock aperture being less than a first outer diameter of the elongate medical device and larger than a second inner diameter of the notch.

19. The method according to claim 15, further including fixedly engaging the sheath, coupled to the clip, relative to the elongate medical device, a distal tip of the sheath extending distally of a distal tip of the elongate medical device.

20. The method according to claim 15, wherein the first grip engages a grip recess disposed in the outer surface of the needle hub when the clip is in the first configuration.

21. The method according to claim 15, wherein the clip is formed as a monolithic piece from one of a plastic, a polymer, a metal, an alloy, or a composite.

22. The method according to claim 15, wherein the elongate medical device includes one of an obturator, a needle, a cannula, a trocar, or a stylet.

23. A method of manufacturing a safety assembly, comprising:
- forming a clip from a first material and transitionable between a first configuration and a second configuration, the clip comprising:
  - a first arm, including a first tab, a first plate, and a first grip, the first tab including a first keyhole aperture;
  - a second arm, including a second tab, a second plate, and a second grip, the second tab including a second keyhole aperture; and
  - an elongate biasing member extending from the first arm to the second arm;
- folding the first tab and the first grip through an angle of 90 degrees relative to the first plate;
- folding the second tab and the second grip through an angle of 90 degrees relative to the second plate;
- forming a sheath from a second material, the sheath including a body defining a lumen and a shroud including a sheath aperture extending therethrough;
- forming a needle hub defining a recess configured to engage the body of the sheath, the shroud configured to engage an outer surface of the needle hub; and
- coupling the clip to the sheath wherein one of the first grip or the second grip extends through the sheath aperture to engage the outer surface of the needle hub when the clip is in the first configuration.

24. The method according to claim 23, further including elastically deforming the elongate biasing member such that the first keyhole aperture axially aligns with the second keyhole aperture.

25. The method according to claim 23, wherein the first material is a sheet of metal and the second material is a polymer.

26. A safety mechanism, comprising:
- an elongate medical device having a shaft extending along a longitudinal axis and defining a first outer diameter, the shaft including a notch extending annularly and defining a second outer diameter, less than the first outer diameter;
- a sheath including a body defining a lumen configured to receive the elongate medical device therethrough, and a shroud extending axially and including a sheath aperture;
- a needle hub defining a recess configured to receive the body of the sheath, the shroud engaging an outer surface of the needle hub; and
- a clip configured to transition between a first configuration and second configuration, the clip comprising:
  - an arm, including a tab, a plate, and a grip, the tab including a keyhole aperture; and
  - a biasing member coupled to the plate and extending annularly about an outer surface of the sheath, and configured to bias the tab towards the second configuration, the elongate medical device extending through first keyhole aperture, the grip extending through the sheath aperture to engage the outer surface of the needle hub when the clip is in the first configuration.

* * * * *